(12) United States Patent
Safai et al.

(10) Patent No.: US 8,094,781 B1
(45) Date of Patent: Jan. 10, 2012

(54) PORTABLE X-RAY BACK SCATTERING IMAGING SYSTEMS

(75) Inventors: Morteza Safai, Seattle, WA (US); William Talion Edwards, Foristell, MO (US); Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 206 days.

(21) Appl. No.: 12/540,239

(22) Filed: Aug. 12, 2009

(51) Int. Cl.
*G01N 23/201* (2006.01)
*G21K 1/00* (2006.01)
*H05G 1/02* (2006.01)

(52) U.S. Cl. ............. 378/87; 378/86; 378/145; 378/197

(58) Field of Classification Search .................... 378/57, 378/58, 70, 86–90, 119, 121, 145, 146, 193, 378/196–198, 203
See application file for complete search history.

(56) References Cited

U.S. PATENT DOCUMENTS

| | | | |
|---|---|---|---|
| 3,737,661 A | 6/1973 | Applegate | |
| 4,277,685 A | 7/1981 | Covic et al. | |
| 4,516,256 A | 5/1985 | Wapperom | |
| 5,237,598 A * | 8/1993 | Albert | 378/98.6 |
| 5,666,393 A | 9/1997 | Annis | |
| 6,292,533 B1 | 9/2001 | Swift et al. | |
| 6,314,157 B1 | 11/2001 | Tachizaki | |
| 6,485,176 B1 * | 11/2002 | Chen et al. | 378/193 |
| 7,050,535 B2 * | 5/2006 | Georgeson et al. | 378/57 |
| 7,463,714 B2 | 12/2008 | Edwards et al. | |
| 7,505,556 B2 | 3/2009 | Chalmers et al. | |
| 7,508,910 B2 | 3/2009 | Safai et al. | |
| 7,526,064 B2 * | 4/2009 | Akery | 378/57 |
| 7,529,343 B2 | 5/2009 | Safai et al. | |
| 2011/0075808 A1 * | 3/2011 | Rothschild et al. | 378/88 |

OTHER PUBLICATIONS

Addicott, "Characterization and Optimization of Radiography by Selective Detection Backscatter X-Ray Imaging Modality", MS Thesis of Nuclear and Radiological Engineering, University of Florida, 2006, 242 pgs.
Allard et al, "Image Processing Techniques for Lateral Migration Radiography Land Mine Images," Technical Report, ARO Grant No. DAAG-55-98-1-0400, University of Florida, Jun. 2000, 80 pgs.
Braith et al., "TPS NDE Backscatter X-Ray Support Tooling Gimbal Assembly" drawings, Jan. 2006, obtained from NucSafe, Inc. engineer, 1 pg.
Dugan et al, "Detection of Land Mines Using Lateral Migration X-ray Radiography," Proc SPIE 48th Annual Meeting, Symposium on Optical Science and Technology, Penetrating Radiation Systems and Applications V, vol. 5199, San Diego, Aug. 2003, 12 pgs.
Dugan et al, "Development and Field Testing of a Mobile Backscatter X-ray Lateral Migration Radiography Land Mine Detection System," SPIE Proc on Detection and Remediation Technologies for Mines and Minelike Targets VII, vol. 4742, Orlando, FL, Apr. 2002, pp. 120-131.

(Continued)

*Primary Examiner* — Anastasia Midkiff
(74) *Attorney, Agent, or Firm* — Caven & Aghevli LLC (57) ABSTRACT

Methods and systems for inspecting objects are disclosed. A portable X-ray backscatter imaging system includes a microfocus X-ray tube to emit X-rays at an object under inspection. A track system rasters the microfocus X-ray tube to inspect the object. A portable hood may enclose the microfocus X-ray tube and the track system against the object A rotation mechanism rotates the microfocus X-ray tube to angle the emitted X-rays at the object. A plurality of solid state detectors receive scattered X-rays to generate an image of the object.

23 Claims, 8 Drawing Sheets

OTHER PUBLICATIONS

Dugan et al., "Lateral Migration Radiography Image Signatures for the Detection and Indentification of Buried Land Mines", Grant Extension Technical Report, Univ of Florida, Jan. 2002, 24 pgs.

Dugan et al,"Status of the XMIS X-ray Backscatter Radiography Land Mine Detection System," SPIE Proceedings on Detection And Remediation Technologies for Mines and Mine like Targets VIII, vol. 5089, Orlando, Apr. 2003, 12 pgs.

Jacobs et al, "Detection/Identification of Land Mines by Lateral Migration Radiography," Proc Second International Conference on the Detection of Abandoned Mines, Institution of Electrical Engineers Publication No. 458, Edinburg, UK, Oct. 1998., pp. 152-156.

Jacobs, "Imaging Subsurface Defects Using X-Ray Lateral Migration Radiography / A New Backscatter Technique," Proceedings of ASNT Conference on Real-Time Radioscopy and Digital Imaging, Aug. 1999, 7 pgs.

Keshavmurthy et al, "Analytical Studies of a Backscatter X-ray Imaging Landmine Detection System," SPIE Proceedings on Detection and Remediation Technologies for Mine and Mine like Targets, vol. 2765-52, pp. 512-525, Apr. 1996.

Neer et al., "Gimbal Assembly" drawings, Oct. 2003, 1 of 2, obtained from NucSafe, Inc. engineer, 1 pg.

Neer et al., "Gimbal Assembly" drawings, Oct. 2003, 2 of 2, obtained from NucSafe, Inc. engineer, 1 pg.

Shedlock et al, "Optimization of a RSD X-Ray Backscatter System for Detecting Defects in the Space Shuttle External Tank Thermal Foam Insulation," Proc SPIE 50th Annual Meeting, Symposium on Optical Science and Technology, Penetrating Radiation Systems And Applications, San Diego, Aug. 2005, 12 pgs.

Shedlock et al, "Preliminary Measurements Supporting Reactor Vessel and Large Component Inspection Using X-Ray Backscatter Radiography by Selective Detection", Proc 2006 International Congress on Advances in Nuclear Power Plants ICAPP, Reno, Jun. 2006, 9 pgs.

Su, "Fundamental Analysis and Algorithms for Development of a Mobile Fast-Scan Lateral Migration Radiography System," Ph.D. Dissertation, University of Florida, May 2001, 132 pgs.

Su et al., "X-ray Lateral Migration Radiography System for the Application of Land Mine Detection," Proceedings of SPIE 45th Annual Meeting, Symposium on Optical Science and Technology, vol. 4142, pp. 150-160, San Diego, Jul. 2000.

Watanabe et al., "Computational Methods for Shape Restoration of Buried Objects in Compton Backscatter Imaging," Nuclear Science and Engineering, vol. 122, pp. 55-67, Jan. 1996.

Wehlburg et al., "Experimental Measurement of Noise Removal Techniques for Compton Backscatter Imaging as Applied to the Detection of Landmines," SPIE Proceedings on Detection and Remediation Technologies for Mine and MinelikeTargets, vol. 2765-51, pp. 502-511, Apr. 1996.

Wehlburg et al., "Geometric Considerations Relating to Lateral Migration Radiography (LMBR) as Applied to the Detection of Landmines," SPIE Proceedings on Detection and Remediation Technologies for Mine and Minelike Targets II, vol. 3079, pp. 384-393, Apr. 1997.

Wehlburg et al, "Image Restoration Techniques Using Compton Backscatter Imaging for Detection of Buried Landmines," SPIE Proc on Detection Technologies for Mine and Minelike Targets, vol. 2496, Apr. 1995, pp. 336-347.

Wells et al., "Lateral Migration Measured Image Signatures in the Detection and Identification of Buried Land Mines", SPIE Proc on Detection and Remediation Technologies for Mines and Minelike Targets IV, vol. 3710, pp. 906-916, Apr. 1999.

American Science and Engineering, "Products and Solutions, Securing Ports, Border Crossings and High Threat Facilities and Events", retrieved Jun. 8, 2009 at http://www.as-e.com/products_solutions/index.asp, 2 pgs.

Nucsafe, "Backscatter Radiography, SXI Scatter X-Ray Imaging", retrieved on Jun. 8, 2009 at http://www.nucsafe.com/cms/Backscatter+Radiography/79.html, 2 pgs.

Rapiscan Systems, retrieved Jun. 8, 2009 at http://rapiscansystems.com, 1 pgs.

Shedlock, "XRay Backscatter Imaging for Radiography by Selective Detection and Snapshot: Evolution, Development, and Optimization", Ph.D. Thesis, The University of Florida, Gainesville, 2007, 98 pgs.

University of Florida, "Scatter X-Ray Imaging (SXI)", retrieved on Jun. 8, 2009 at http://sxi.nre.ufl.edu, 1 pg.

Wikipedia, "Backscatter X-Ray", retrieved on Jun. 8, 2009 at http://en.wikipedia.org/wiki/Backscatter_X-ray, 2 pgs.

\* cited by examiner

PORTABLE X-RAY BACK SCATTERING IMAGING SYSTEMS

TECHNICAL FIELD

The present disclosure pertains to inspecting objects, and more specifically, inspecting objects using portable X-ray Back Scattering imaging systems.

BACKGROUND

In some situations, various objects such as aircraft vehicles call for inspection at one or more generally known locations. For example, if a vehicle were to sustain an impact such as during a collision of two vehicles, it may be desirable to inspect one or both of the impacted vehicles at the impact location which generally can be determined by observing the impact or by a post-collision examination of the vehicles. At other times, statistical data may call for inspection of a group of objects at one or more generally known location. In situations where visual inspection cannot easily or adequately inspect the objects such as to determine whether or not there is internal structural damage after an impact, an alternative method of inspection is desirable.

Examples of vehicle objects that may call for inspection include aircraft, maritime vessels, automobiles, and other large investment assemblies. Examples of structure objects that may call for inspection include petrochemical facilities, power generation facilities, nuclear facilities, water treatment plants, etc. Effective inspection of such vehicle and structure objects may advantageously extend the operational lifespan of the objects.

One technique frequently used to inspect features or characteristics of an object at a generally known location includes disassembling the object in order to access interior elements. Although disassembly provides access to interior surfaces that are otherwise difficult to inspect, this technique is often time consuming and expensive.

Another technique for inspecting features or characteristics of an object includes using an application of ultrasonics. For example, pulse echo ultrasonics may be used to assess impact damage to the skin of various vehicles or structures; however, the ultrasonic method cannot assess impact damage to nearby stiffeners when the damage occurs further into the stiffener than can be interrogated with the pulse echo ultrasonics.

An alternative technique for inspecting features or characteristics of an object at a generally known location utilizes X-ray Back Scattering imaging. X-ray Back Scattering imaging involves generating images of the object using an X-ray imaging system. One advantage of X-ray Back Scattering imaging is that it reduces inspection time and costs since it may not require disassembly in order to inspect interior elements.

Traditional X-ray imaging and X-ray Back Scattering systems are often large cumbersome systems. For example, traditional X-ray imaging systems generally require large 160 kilovolt X-ray tubes hooked up to a large high voltage power supply. As a result of the large X-ray tube and power supply, such systems generally require cooling to prevent overheating. In general, it is not uncommon for such systems to weight up to 1000 pounds making them very cumbersome.

SUMMARY

Methods and systems to inspect objects using portable X-ray Back Scattering imaging systems are disclosed. In one embodiment, a portable X-ray backscatter imaging system may include a light weight low radiation microfocus X-ray tube to emit X-rays through a stationary aperture of the portable X-ray backscatter system. The stationary aperture of the portable X-ray backscatter system then directs the X-rays generally toward an object under inspection. A rotation mechanism may rotate the microfocus X-ray tube about a yaw axis to angle the emitted X-rays at the object. A plurality of solid state detectors may receive one or more scattered X-rays to generate an image of the object. The system may also include a track system to raster at least the microfocus X-ray tube. A portable hood may enclose the microfocus X-ray tube and the track system against the object.

In another embodiment, a method of inspecting a structure for internal damage includes attaching an X-ray Back Scattering imaging system to the structure at a potentially damaged area of the structure. A plurality of motors raster a microfocus X-ray tube of the X-ray Back Scattering imaging system to inspect the structure. Scattered X-rays are received from the structure to generate an image of the structure.

In a further embodiment, a system for performing vehicle inspection includes a portable X-ray backscatter imaging unit. A microfocus X-ray tube of the portable X-ray backscatter imaging unit emits X-rays at the vehicle and a track system rasters at least the microfocus X-ray tube. A portable hood may enclose the microfocus X-ray tube and the track system against the vehicle.

The features, functions, and advantages may be independently achievable in various embodiments of the present disclosure or combinable in yet other embodiments.

BRIEF DESCRIPTION OF THE DRAWINGS

The detailed description is described with reference to the accompanying Figures. In the Figures, the left-most digit(s) of a reference number identifies the Figure in which the reference number first appears. The same reference numbers in different Figures indicate similar or identical items.

DETAILED DESCRIPTION

Overview

As discussed above, although X-ray Back Scattering imaging may advantageously enable nondestructive inspection of objects, further improvements are desirable. Techniques for further improving object inspection are disclosed herein. Some techniques include using a portable X-ray backscatter system consisting of a microfocus X-ray tube to inspect the object. Other techniques involve attaching the X-ray backscatter system to the object. In addition, a track system may enable X-Y rastering of the microfocus X-ray tube to generate an X-ray image of the object. The portable X-ray backscatter system may be yawed to a pre-selected angle to raster the microfocus X-ray tube at the pre-selected angle. A portable hood may surround the entire X-ray Back Scattering imaging system including the track system. As discussed herein, the techniques may be implemented on vehicles or structures, which includes without limitation, aircraft, maritime vessels, spacecraft, motor vehicles, mechanical devices, petrochemical facilities, power generation facilities, nuclear facilities, water treatment plants, and other structures of or machines that receive maintenance.

Illustrative System

Figure 1:
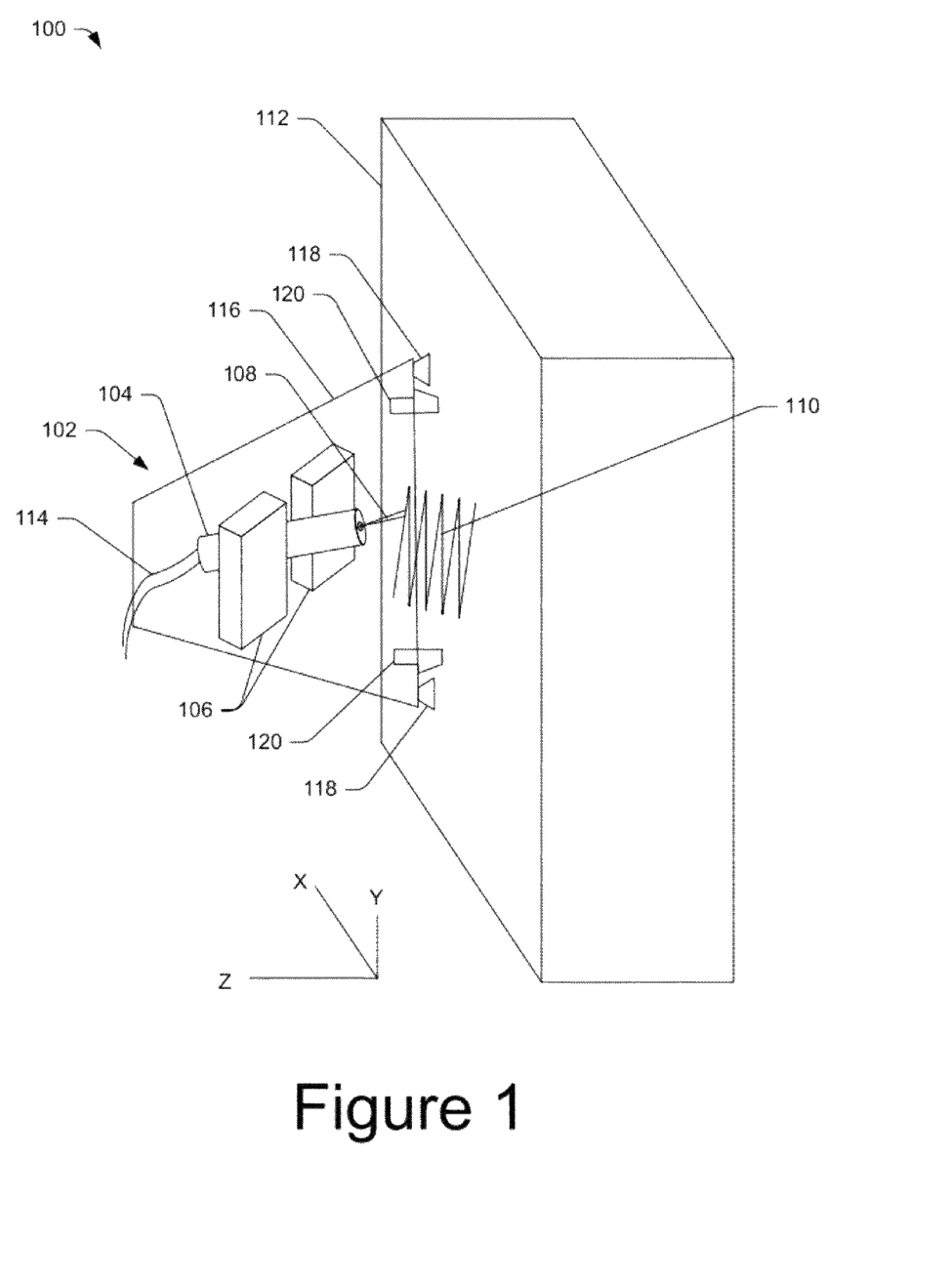
FIG. 1 is an isometric schematic diagram of an illustrative portable X-ray Back Scattering imaging system.

FIG. 1 is an isometric schematic diagram 100 of an illustrative portable X-ray Back Scattering imaging system 102 in an operational environment. In one embodiment, the portable X-ray imaging system 102 is an X-ray backscatter system. An X-ray backscatter system may be advantageous over transmission λ-ray systems since X-ray backscatter systems can inspect structures from one side since the means of X-ray generation and detection can be placed on the same side. Another advantage is that X-ray backscatter typically projects less radiation than a transmission λ-ray system and so requires a smaller exclusion area for radiation safety. As illustrated in FIG. 1, the portable X-ray Back Scattering imaging system 102 may include a small filament microfocus X-ray tube 104. Since microfocus X-ray tubes are smaller in size than conventionally X-ray backscatter systems, the microfocus X-ray tube portable X-ray imaging system 102 does not require cooling during operation. In addition, microfocus X-ray tubes 104 are generally low in radiation leaking and have a small X-ray field of view 108. The microfocus X-ray tubes 104 may be rastered 110 in the X-Y direction as illustrated in FIG. 1. A track system such as the track system described below with reference to FIG. 2 advantageously allows rastering 110 of the microfocus X-ray tube 104 while eliminating the need to use a rotating aperture such as used in conventional X-ray backscatter systems.

The microfocus X-ray tube 104 inspects an object 112 by projecting an X-ray field of view 108 onto the object. As the microfocus X-ray tube 104 generates X-rays, the X-rays may pass through one or more stationary apertures (not shown) to generate the X-ray field of view 108. The small filament of the microfocus X-ray tube 104 allows for generation of a more collimated X-ray field of view 108 than the conventional large kilovolt X-ray tubes. The portable X-ray Back Scattering imaging system 102 may move the X-ray field of view 108 about an inspection object 112 using a rotational mechanism as described further below with reference to FIG. 3. Any power source may supply power to the microfocus X-ray tube 104 via a power cord 114. One or more solid state detectors 106 of the portable X-ray Back Scattering imaging system 102 may receive at least a portion of the X-rays as they are scattered from the object 112 to generate an image of the object.

The microfocus X-ray tube 104 may use any technique well known in the art to generate the X-rays. In one or more embodiments, the microfocus X-ray tube 104 is a vacuum tube and includes a cathode to emit electrons into the vacuum. An anode collects the electrons emitted from the cathode to establish an electrical current through the microfocus X-ray tube 104. To generate the X-rays, electrons are boiled off the cathode and collide with the anode under a high energy electric field. If the colliding electrons have sufficient energy, they can knock an electron out of an inner shell of the target metal atoms. X-ray photons with precise energies are emitted when electrons from higher states drop down to fill the vacancy created when the electron is knocked out of the inner shell.

A hood 116 may surround at least the microfocus X-ray tube 104 as illustrated in FIG. 1 to form the portable X-ray Back Scattering imaging system 102. In one embodiment, the portable X-ray Back Scattering imaging system 102 attaches to the object 112 such that the object is on one side of the microfocus X-ray tube 104 while the hood 116 surrounds the microfocus X-ray tube 104 on all the other sides. The portable X-ray Back Scattering imaging system 102 may utilize any attachment mechanism 118 to attach to the object 112. For example, the portable X-ray Back Scattering imaging system 102 may use a suction mechanism such as vacuum assisted suction cups as illustrated in FIG. 1 to attach to the object 112. Alternatively, the attachment mechanism 118 may include clamps, bolts, tape, magnets, or screws to attach the portable X-ray Back Scattering imaging system 102 to the object 112. Alternatively, the hood 116 including the portable X-ray Back Scattering imaging system 102 may be mounted on a stand or robotic arm (not shown).

As further illustrated in FIG. 1, a safety interlock 120 may ensure a proper attachment of the portable X-ray Back Scattering imaging system 102 to the object 112. The safety interlock 120 links to the microfocus X-ray tube 104 such that the safety interlock is able to communicate with the microfocus X-ray tube. For example, the safety interlock 120 may communicate an attachment indication (whether or not the portable X-ray Back Scattering imaging system 102 is properly attached to the object 112 to the microfocus X-ray tube 104. If the safety interlock 120 communicates an attachment failure communication (communication indicating that the portable X-ray Back Scattering imaging system 102 is not properly attached to the object 112), the microfocus X-ray tube may be prevented from inspecting the object. In a further embodiment, the microfocus X-ray tube 104 may be prevented from generating the X-rays Back Scattering until the safety interlock 120 communicates an attachment pass communication (communication indicating that the portable X-ray Back Scattering imaging system 102 is properly attached to the object 112). If the portable X-ray imaging system 102 becomes unattached from the object 112 while the microfocus X-ray tube 104 is operatively emitting X-rays, an attachment failure communication may automatically shut off the microfocus X-ray tube. If the portable X-ray imaging system 102 becomes properly attached to the object 112, an attachment pass communication may automatically commence a generation of X-ray beams from the microfocus X-ray tube 104.

The safety interlock 120 may be any mechanism that identifies an attachment of the portable X-ray Back Scattering imaging system 102 with the object 112. For example, the safety interlock 120 may be a mechanical plunger switch, an optical interlock, a proximity sensor, and so forth.

Although FIG. 1 illustrates the hood 116 having a trapezoidal shape, the hood may be of any shape so long as it is open on one end and able to surround the microfocus X-ray tube 104. For example, the hood 116 may be cone-shaped or cube-shaped. In one embodiment, the hood 116 is made of lead material such that it is non-transparent.

The hood 116 may include adjustable legs 306 (not shown) to adjust a distance of the hood relative to the object 112. The adjustable legs 306 may be of any adjustable mechanism as well known in the art. For example, the adjustable legs 306 may be telescoping legs. Expanding the length of the adjustable legs 306 can alters a distance of the microfocus X-ray tube 104 to the object 112. As illustrated in FIG. 1, the small size of the microfocus X-ray tube 104 allows the portable X-ray Back Scattering imaging system 102 to be positioned close to the object. Being close to the object 112 advantageously enables the portable X-ray imaging system 102 to capture low energy X-ray images of the object at equivalent resolution levels to the X-ray images captured by the high energy X-ray Back Scattering imaging systems. For example, the portable X-ray imaging system 102 may perform close-proximity nondestructive testing such as water detection in honeycombed structure or corrosion detection in subsurface of the aluminum skin and/or composites structures.

Illustrative Track System

Figure 2:
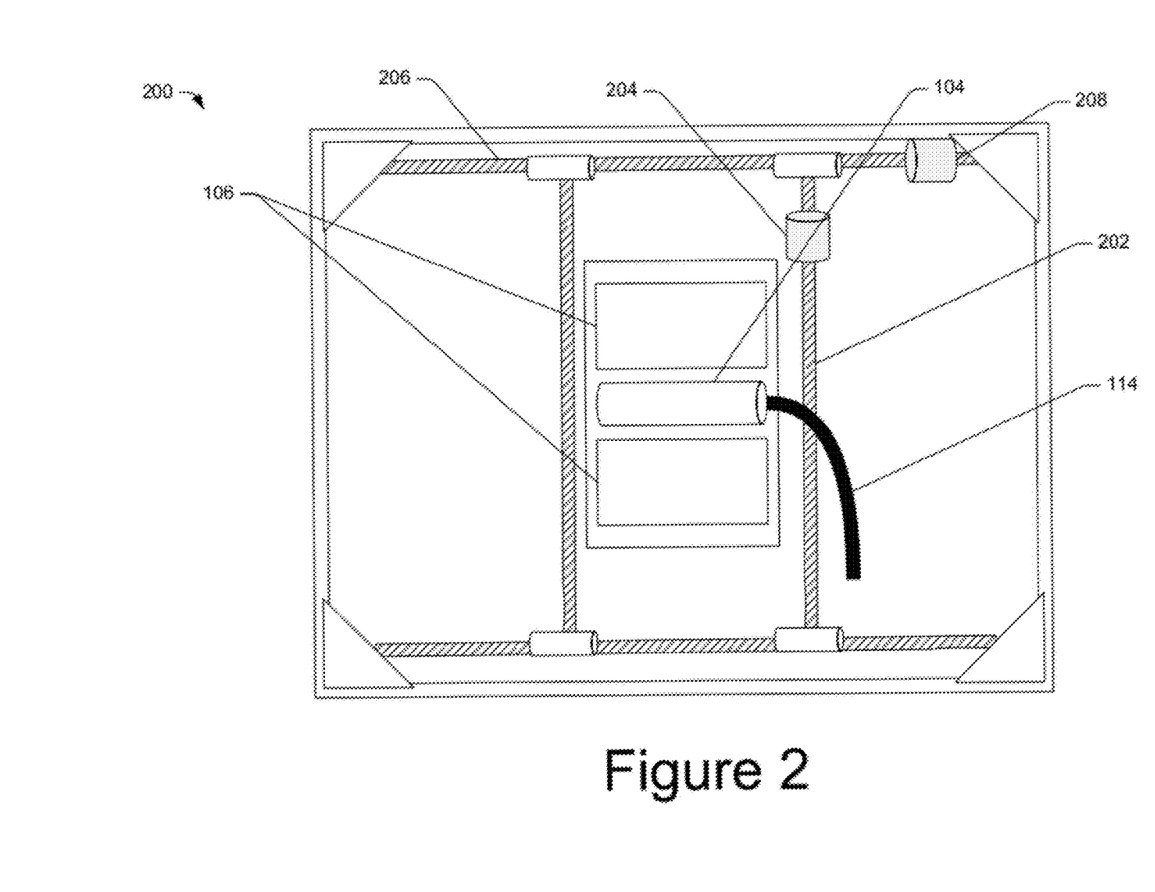
FIG. 2 is a top view schematic diagram of an illustrative track system for a portable X-ray Back Scattering imaging system.

FIG. 2 is a top view schematic diagram of an illustrative track system 200 for a portable X-ray Back Scattering imaging system 102. As mentioned above, the small filament of the microfocus X-ray tube 104 is advantageous for various reasons including enabling an X-Y rastering of the microfocus X-ray tube.

Any conceivable translational mechanism may enable the rastering of the microfocus X-ray tube 104. In one embodiment, as illustrated in FIG. 2, a plurality of threaded rod elements enable the rastering of the microfocus X-ray tube 104 by moving the microfocus X-ray tube along an X-axis and a Y-axis of the track system 200. As illustrated in FIG. 2, the microfocus X-ray tube 104 is attached to at least a first threaded rod element 202. An X-direction motor 204 may rotate at least the first threaded rod element 202 such that as the first threaded rod element rotates, the microfocus X-ray tube 104 moves along an X-axis. The microfocus X-ray tube 104 may attach to at least a second threaded rod element 206 such that as a Y-direction motor 208 rotates the second threaded rod element 206, the microfocus X-ray tube 104 moves along a Y-axis.

The X-direction motor 204 and the Y-direction motor 208 may be of any motor types. For example, the X-direction motor 204 and the Y-direction motor 208 may be computer-controlled smart motors. In some situations, the X-direction motor 204 and the Y-direction motor 208 move the microfocus X-ray tube 104 along both the X-axis and the Y-axis at the same time. In other situations, the X-direction motor 204 may only be used to move the microfocus X-ray tube 104 along just the X-axis. Similarly, the Y-direction motor 208 may be used to move the microfocus X-ray tube 104 along just the Y-axis.

As discusses above with respect to FIG. 1, one or more solid state detectors 106 may receive at least a portion of the X-rays as they are scattered from an object to generate an image of an object under inspection. In one embodiment, the track system 200 moves the solid state detectors 106 move along with the microfocus X-ray tube 104 regardless of the direction in which the microfocus X-ray tube is moving. Alternatively, the track system 200 may move the solid state detectors 106 along with the microfocus X-ray tube 104 only when the microfocus X-ray tube moves along the X-axis. In such an embodiment, if the track system 200 moves the microfocus X-ray tube 104 along the Y-axis, then the microfocus X-ray tube moves independently from the solid state detectors 106 while the solid state detectors remain stationary.

The track system 200 may raster the microfocus X-ray tube in an X-Y direction as noted above. In one embodiment, the track system 200 rasters the microfocus X-ray tube 104 while the solid state detectors 106 operatively receive at least a portion of the X-rays as they are scattered from an object. The images of the object may be generated at every point in time and for every position along the track system for each detector. These images can be overlayed to increase contrast without reducing the scan speed. If the detectors 106 are placed in different planes relative to each other, parallax between images can be produced in the reconstruction that can be used to provide depth information with simple measurements.

The track system may be attached to a hood (not shown) such that the hood surrounds at least the track system 200 and the microfocus X-ray tube 104 on all sides except for the side that the hood attaches to an object. Any mechanism may attach the track system 200 to a hood. For example, the hood may include a guide rail such that the track system 200 slides into the hood and clamps into place. Alternatively, the track system 200 may bolt to or screw into the hood.

Illustrative Rotation Mechanism

Figure 3:
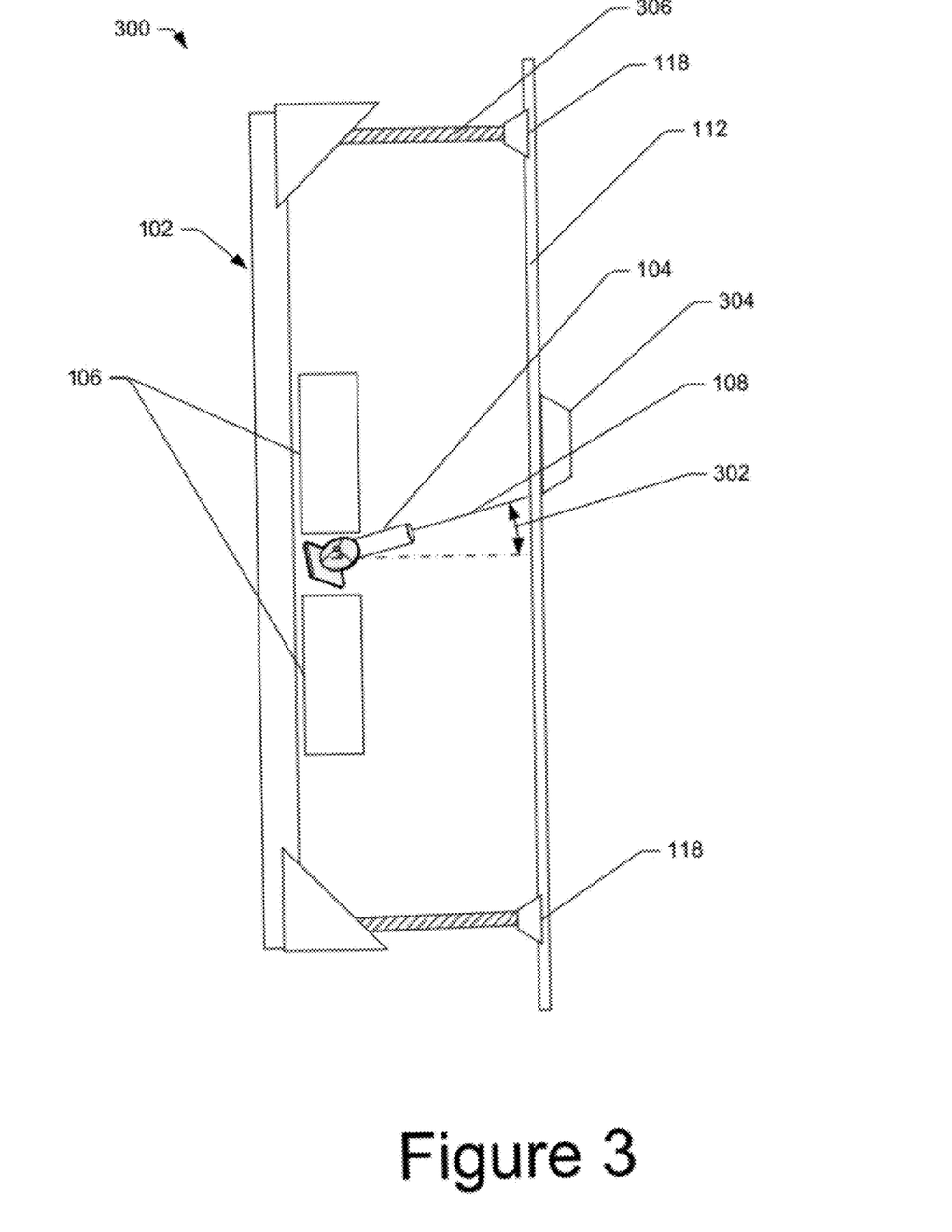
FIG. 3 is a side view schematic diagram of an illustrative rotational mechanism for a portable X-ray Back Scattering imaging system.

FIG. 3 is a side view schematic diagram 300 of an illustrative rotational mechanism for a portable X-ray Back Scattering imaging system. As mentioned above, a rotational mechanism may move the X-ray field of view 108 about an inspection object 112. The rotational mechanism may rotate the microfocus X-ray tube 104 about a yaw axis (not shown) to move the X-ray field of view 108 about an inspection object. Specifically, rotating the microfocus X-ray tube may alter the angle 302 at which the emitted X-rays impinge upon the object 112.

The rotation mechanism may rotate one or more elements of the portable X-ray imaging system about the yaw axis to any angle within a 360 degree range. In one embodiment, the rotation mechanism rotates at least the microfocus X-ray tube 104 and the solid state detectors 106 about the yaw axis. Alternatively, the rotation mechanism rotates at just the microfocus X-ray tube 104 about the yaw axis.

In one embodiment, a motor may rotate the one or more elements of the portable X-ray imaging system about the yaw axis to any desired angular orientation within a 360 degree range. The motor may rotate the one or more elements of the portable X-ray Back Scattering imaging system while the X-ray imaging system is operatively imaging the object 112 such that a continuous image of the object is generated. In such an embodiment, a power source does not have to be disconnected from the X-ray imaging system in order to rotate the elements about the yaw axis.

The combination of the roll mechanism of FIG. 3 with the track system illustrated in FIG. 2 advantageously allows the microfocus X-ray tube 104 to rotate continuously through a selected fan angle at each position along an X axis to scan X-rays across the object 112 to produce an image. Alternatively, the angle 302 may be a set to a specific pre-selected angle such that the track system performs rastering in the X-Y direction at the pre-selected yaw angle. Rastering the microfocus X-ray tube 104 in the X-Y direction at the pre-selected yaw angle advantageously allows the portable X-ray Back Scattering imaging system 102 to take advantage of the particular geometry of the inspection object in order to obtain an image of the structure that is most likely to show desired features or elements. For example, if the user of the portable X-ray Back Scattering imaging system 102 is inspecting the object 112 for specific features such as delamination damage in a hat stiffener 304, it may be desirable to aim the microfocus X-ray tube 104 (and transmitted X-ray field of view 108) at a specific angle that the portable X-ray imaging system 102 is sensitive to finding disbond damage. The track system may then perform rastering in the X-Y direction to inspect for delamination damage.

As further illustrated in FIG. 3, an attachment mechanism 118 may attach the portable X-ray Back Scattering imaging system 102 to the object 112. For example, as illustrated in FIG. 3, a suction mechanism such as vacuum assisted suction cups may attach the portable X-ray Back Scattering imaging system 102 to the object. The portable X-ray Back Scattering imaging system 102 may include adjustable legs 306 to adjust a distance of the portable X-ray Back Scattering imaging system 102 to the object 112. The adjustable legs 306 may be any adjustable mechanism such as telescoping legs.

Illustrative Implementation

Figure 4:
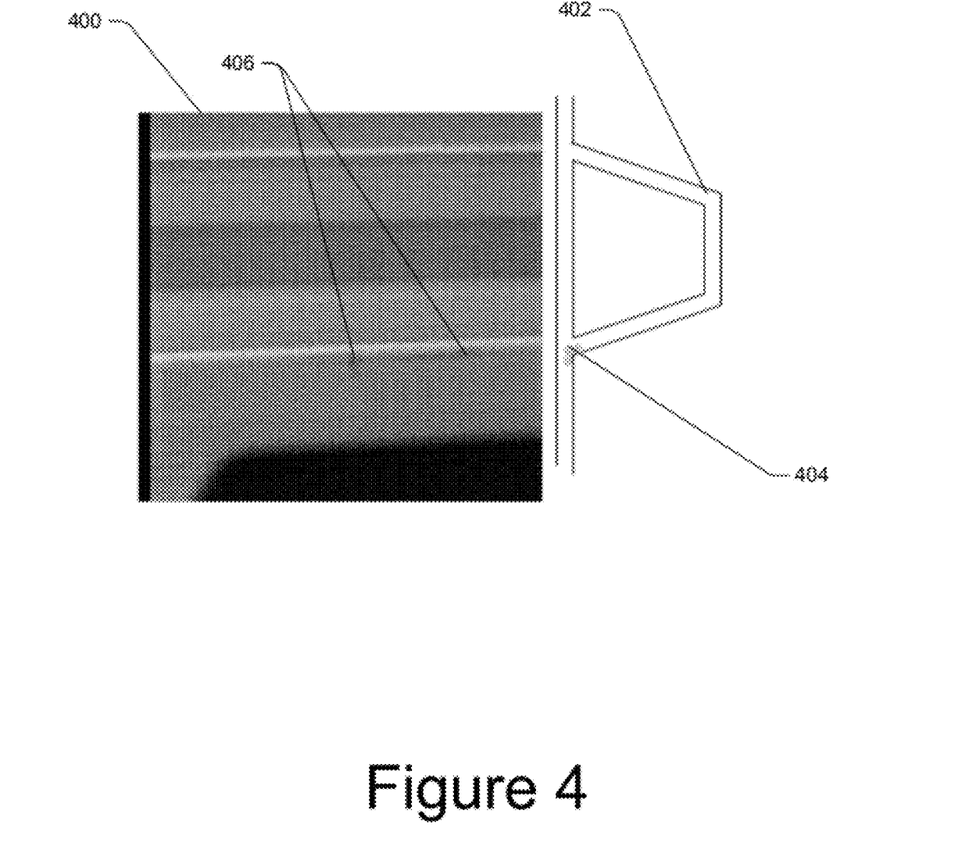
FIG. 4 is an illustrative X-ray Back Scattering imaging system image.

As mentioned above with respect to FIG. 1, the combination of the roll mechanism with the track system advantageously allows the microfocus X-ray tube to perform rastering in the X-Y direction at the pre-selected yaw angle to take advantage of the particular geometry of the structure to be inspected. FIG. 4 shows an illustrative image 400 generated by an illustrative portable X-ray Back Scattering imaging system. In FIG. 4, the portable X-ray Back Scattering imaging system inspected an aircraft fuselage hat stiffener 402 to search for substructural damage 404 after an impact. The image 400 shows hat stiffener impact damage 406 that cannot be seen from the skin side with traditional inspection methods. The portable X-ray imaging system advantageously inspected the structure without having to dissemble to aircraft.

Figure 5:
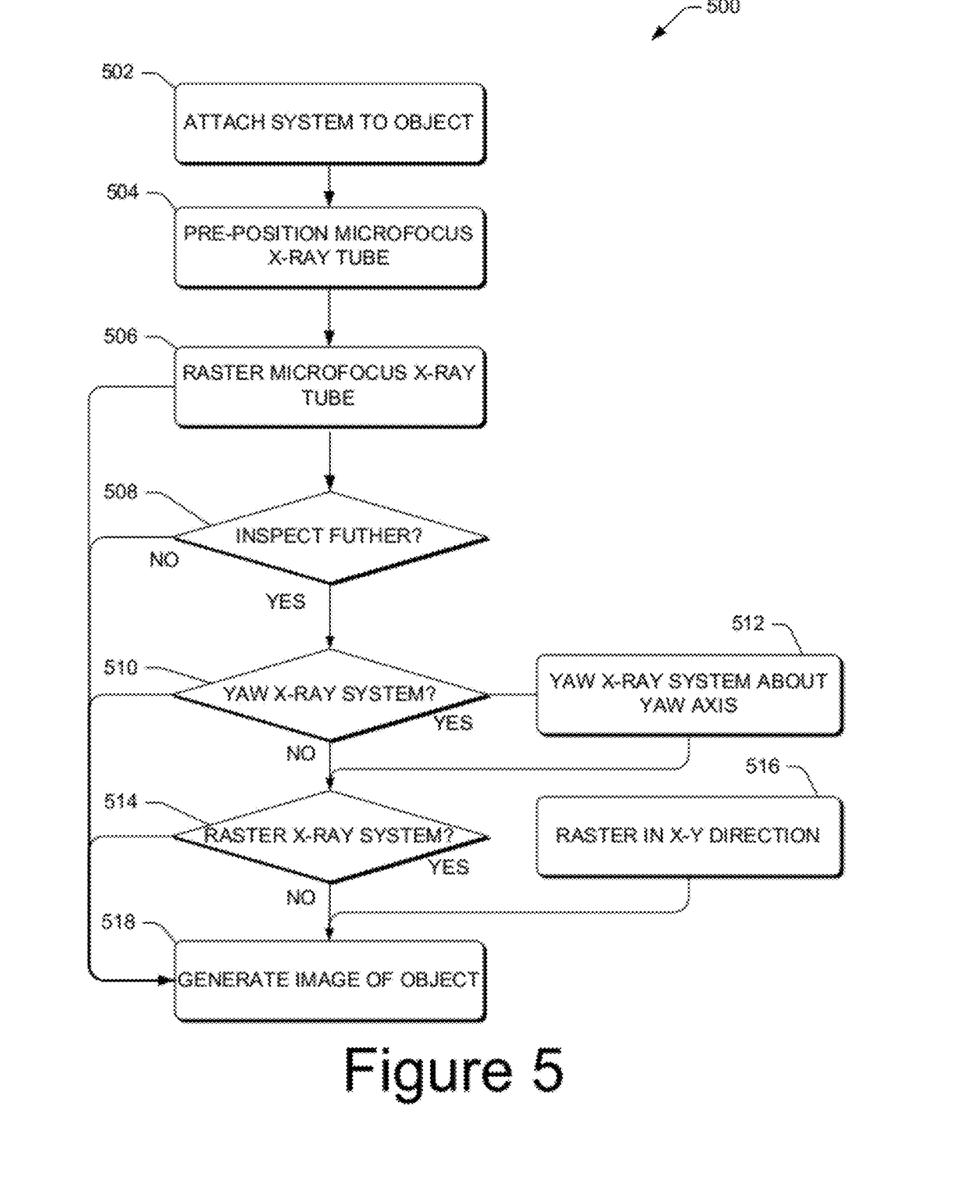
FIG. 5 is a flow diagram of an illustrative operational embodiment of the portable X-ray Back Scattering imaging system.

FIG. 5 is an illustrative operational embodiment 500 of a portable X-ray backscatter system. The operational embodiment 500 is illustrated as a collection of blocks in a logical flow graph, which represent a sequence of operations that can be implemented in hardware, software, or a combination thereof. In the context of software, the blocks represent computer-executable instructions that, when executed by one or more processors, cause the one or more processors to perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process.

The process 500 may be performed, at least in part, by the portable X-ray imaging system of FIG. 1. At 502, the portable X-ray backscatter system attaches to an inspection object. Attaching the portable X-ray backscatter system to the object may include attaching a portable hooded X-ray imaging system including a track rack unit to the object. The portable X-ray backscatter system may attach to the object using a plurality of vacuum assisted suction cups as described above with reference to FIG. 3. The portable X-ray backscatter system preferably attaches to the object at a predetermined location such as at a location of a known hat stiffener to inspect structural features of the hat stiffener. The portable X-ray Back Scattering imaging system may automatically determine the predetermined location by examining the geometry of the object and sensing its location relative to the object. Alternatively, a user may input the predetermined location.

At 504, a microfocus X-ray tube of the portable X-ray backscatter system is linearly and/or rotationally prepositioned. A translational mechanism such as the track system described above with reference to FIG. 2 may linearly preposition the microfocus X-ray tube to a desired X and Y location. A rotation mechanism may preposition the microfocus X-ray tube to a desired angle based on known specific features of the object such that the portable X-ray backscatter system can perform optimum feature assessment of the object. In one embodiment, a user operates a mechanism, such as a remote control linked to the track system and the rotation mechanism, to translate the microfocus X-ray tube to the desired location on the track system and/or rotate the microfocus X-ray tube to the desired angle. Alternatively, as described further below with reference to FIGS. 6 and 7, the portable X-ray backscatter system may include a scanner alignment control system to translate the microfocus X-ray tube to an ideal location on the track system and/or rotate the microfocus X-ray tube to an ideal angle based on analyzing a digital model of the object.

At 506 the portable X-ray backscatter system operably performs rastering in an X-Y direction at the desired angle. A track system may move at least the microfocus X-ray tube in the X-Y direction using one or more motors. The motors may be remotely operable such that a user can initiate the rastering while the X-ray backscatter system remains enclosed by a hood. Alternatively, the X-ray backscatter system may sense its location relative to the object and automatically perform the rastering with minimal or no user interaction. In one embodiment, a safety mechanism may prevent the X-ray backscatter system from becoming operational if the X-ray backscatter system is not properly hooded. For example, the safety mechanism may use a safety interlock method as described above with reference to FIG. 1.

At 508, a determination is made as to whether the rastering performed at 506 generated the desired image of the object. A user may make the determination at 508 based on examination of a backscatter image generated from block 506. Alternatively, the portable X-ray backscatter system may automatically make the determination at 508 by sensing a position of the portable X-ray backscatter system relative to the object. The portable X-ray backscatter system may use a stored schematic diagram of the object to aid in automatically making the decision at 508.

If more areas of the object are to be inspected (i.e., the "Yes" branch from 508), a determination is made at 510 whether the additional elements of the object can be inspected by yawing at least a portion of the portable X-ray backscatter system using the rotation mechanism described with reference to block 504. If so (i.e., the "Yes" branch from 510), the rotation mechanism yaws at least a portion of the portable X-ray backscatter system about a yaw axis at 512. In one embodiment, the rotation mechanism yaws only the microfocus X-ray tube about the yaw axis at 512. Alternatively, the rotation mechanism yaws the microfocus X-ray tube as well as one or more detectors about the yaw axis at 512 In one operational mode, the rotation mechanism rotates at least the microfocus X-ray while the portable X-ray backscatter system operatively images the object.

Regardless of whether yaw is used (i.e., from 512) or is not used to capture other parts of the objects (i.e., the "No" branch from 510), a determination is made whether a rastering of at least the microfocus X-ray tube in the X-Y direction along the track system enables additional inspection of the object. If so (i.e., the "Yes" branch from 514), the portable X-ray backscatter system moves along the track system. In the described implementation above, an X-direction motor and a Y-direction motor rasters at least the microfocus X-ray tube along the track system using a plurality of threaded rod elements.

In one embodiment, the portable X-ray backscatter system simultaneously yaws at 512 and moves at 516. In an alternative embodiment, the portable X-ray backscatter system independently yaws at 512 and independently moves at 516.

At least a portion of the emitted X-ray beam scatters back off the object to generate an image of the object at 518.

Illustrative Scanner Alignment Control System

Figure 6:
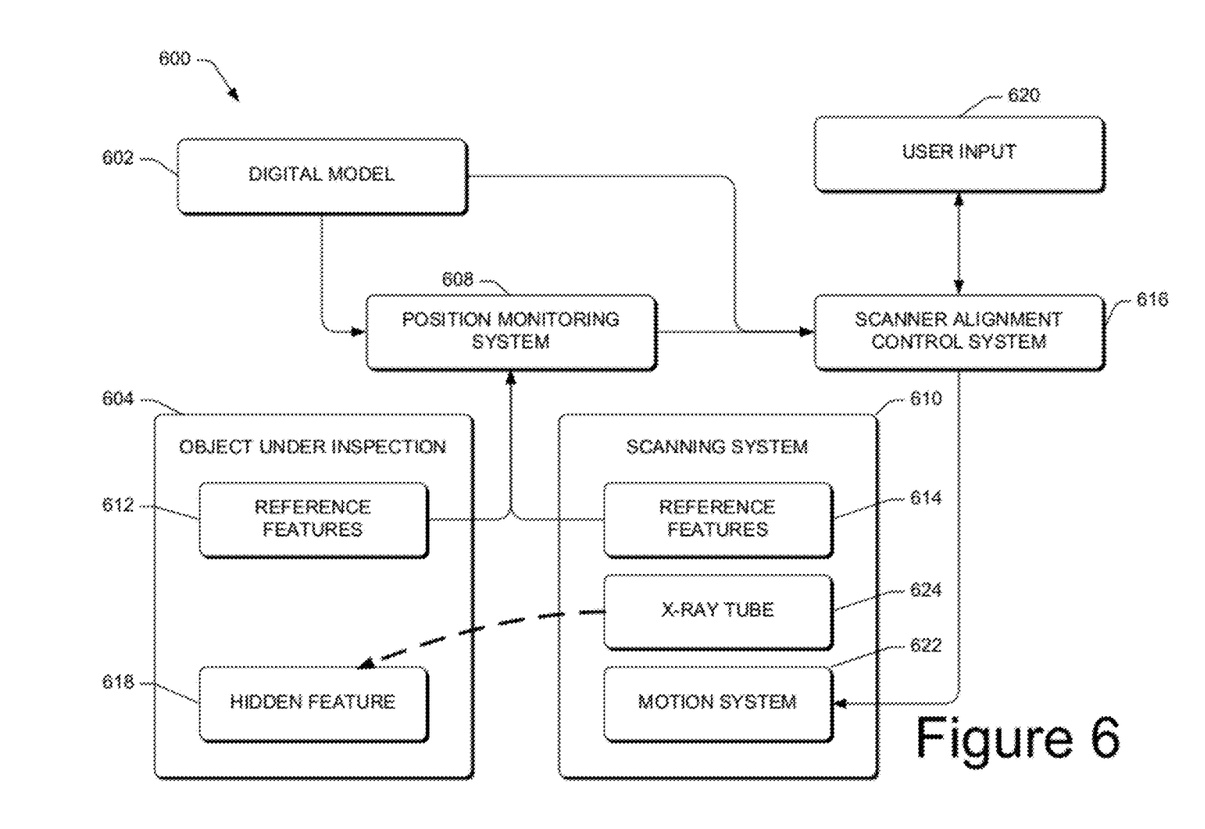
FIG. 6 is a flow diagram for an illustrative scanner alignment control system.
Figure 7:
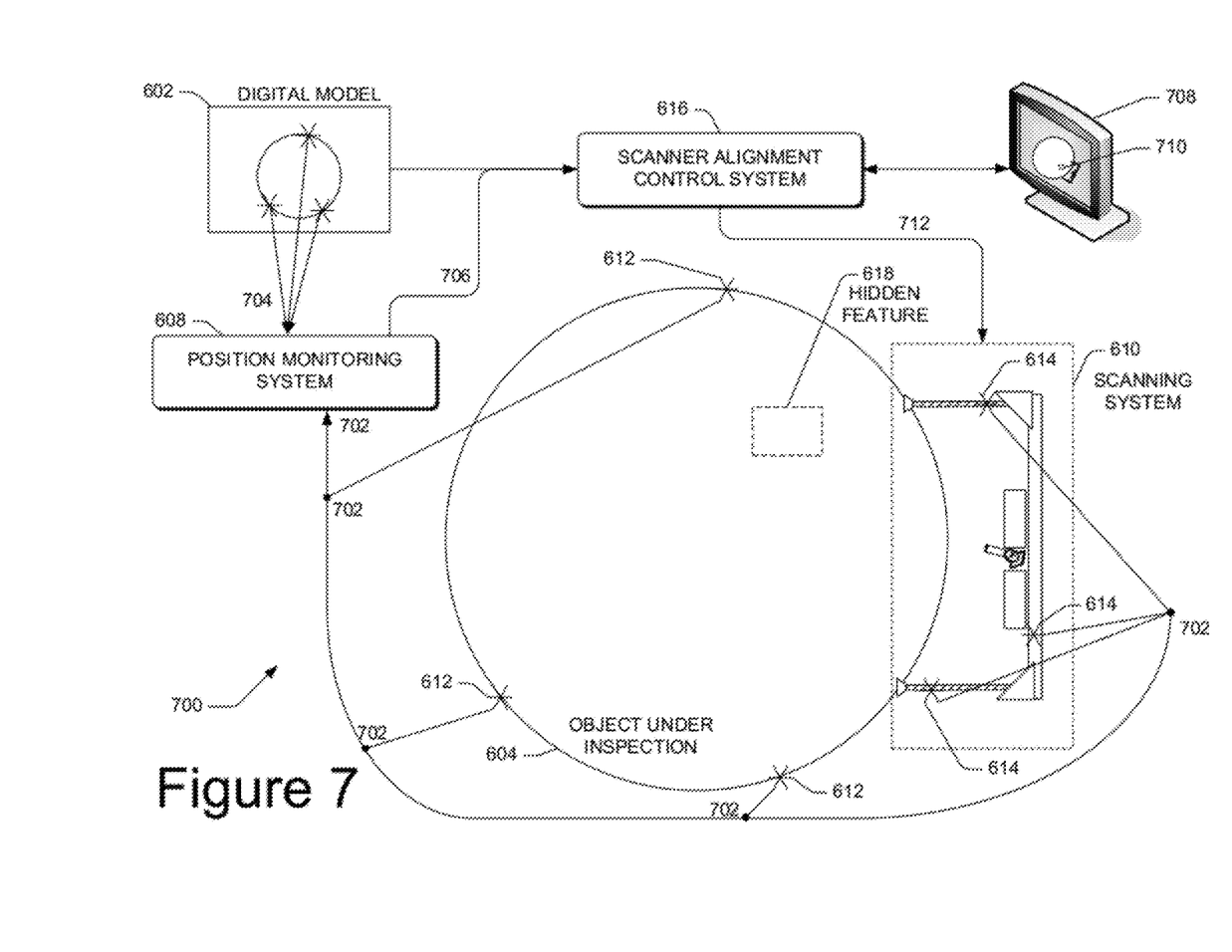
FIG. 7 is a combined hardware and flow diagram for an illustrative scanner alignment control system.

FIGS. 6 and 7 together illustrate an exemplary scanner alignment control system to position a microfocus X-ray tube. FIG. 6 is a flow diagram 600 for an illustrative scanner alignment control system. FIG. 7 is a combined hardware and flow diagram 700 for an illustrative scanner alignment control system. FIGS. 6 and 7 are described together. The elements illustrated in FIGS. 6 and 7 represent operations that may be implemented in hardware, software, or a combination thereof. In the context of software, the elements represent computer-executable instructions that, when executed by one or more processors, cause the one or more processors to perform the recited operations. Generally, computer-executable instructions include routines, programs, objects, components, data structures, and the like that perform particular functions or implement particular abstract data types. The order in which the operations are described is not intended to be construed as a limitation, and any number of the described elements can be combined in any order and/or in parallel to implement the process.

As mentioned above with respect to FIG. 5, the portable X-ray backscatter system may include a scanner alignment control system to translate the microfocus X-ray tube to an ideal location on the track system and/or rotate the microfocus X-ray tube to an ideal angle based on analyzing a digital model of the object. The ability to automatically translate and/or rotate the microfocus X-ray tube to the ideal position based on a digital model of the object advantageously aims the microfocus X-ray tube directly at a desired feature of the object without having to perform trial and error even if there is no direct line of sight between the microfocus X-ray tube and desired feature.

With reference to FIG. 6, a digital model 602 containing data relating to an object under inspection 604 is provided. The digital model 602 may include interior and exterior data, such as the mass that defines the interior and exterior surfaces. The data in the digital model 602 may be in a coordinate system specific to the object under inspection 604. For example, if the object under inspection 604 is an aircraft, the data in the digital model may be in an aircraft coordinate system. A position monitoring system 608 may generate a virtual representation of a scanning system 610, such as the illustrative portable X-ray Back Scattering imaging system 102 of FIG. 1, such that the virtual representation of a scanning system is in the same coordinate system as the digital model of the object.

The position monitoring system 608 may use object reference features 612 measurements, scanner reference features 614 measurements, and known locations of the object reference features (provided via the digital model 602) to set the scanning system and the object to a common reference coordinate system. For example, element 702 of FIG. 7 illustrates the position monitoring system using various object reference features 612 as well as various scanner reference features 614 to generate the virtual representation of the scanning system 610. Although FIG. 7 only illustrates three object reference features 612 and three scanner reference features 614, it is appreciate that many more reference features may be used to generate a comprehensive virtual representation of the scanning system 610. Element 704 of FIG. 7 illustrates that the position monitoring system 608 is also provided with known locations of the object reference features 612. In one embodiment, the object under inspection 604 is an aircraft and the object reference features 612 are golden rivets located throughout the aircraft and identified in the structural repair manual.

The position monitoring system 608 may perform a best fit analysis of the scanner reference features 614 to the object reference features 612 to generate the virtual representation of the scanning system 610. The position monitoring system 608 may export the virtual representation of the scanning system 610, illustrated by line 706 of FIG. 7, to a scanner alignment control system 616. The scanner alignment control system 616 may then combine the virtual representation of the scanning system 610 with the digital model 602 of the object under inspection 604. It is appreciated that without the best fit analysis of the position monitoring system 608, a digital representation of the scanning system 610 would render the scanning system floating out in space since there would be no common reference to link the scanning system with the object.

As Illustrated in FIG. 7, the scanner alignment control system may display the virtual representation of the scanning system 610 together with the digital model 602 of the object under inspection 604 on an interactive display device 708. An operator of the interactive display device may then select a hidden feature 618 of the object to inspect (i.e. element 620 of FIG. 6). Since the operator is selecting the desired location using a digital model of the object, it is appreciated that the operator may easily select any feature of the object including features which are not visible from the exterior surface of the object such as virtually represented hidden feature 710 of FIG. 7. For example, an operator may employ common tools available for interacting with digital models such as zooming, panning, etc. . . . to locate the hidden feature on the display device and then the operator could select the hidden feature on the display device by clicking on it. In response to the user input, the scanner alignment control system 616 may send a command (line 712 in FIG. 7) to a motion system 622 of the scanning system 610 instructing the scanning system to aim a microfocus X-ray tube 624 of the scanning system 610 at the hidden feature 618. In a situation where the scanner reference features 614 are located on a track system of the scanning system 610 and not on the microfocus X-ray tube itself, such as illustrated in FIG. 7, the scanning system may still accurately aim the microfocus X-ray tube at the hidden feature 618 by taking into account any differences between the location scanner reference features with respect to the location of the microfocus X-ray tube.

Although FIGS. 6 and 7 illustrate the position monitoring system 608 and the scanner alignment control system 616 being separate elements, it should be appreciated that one element may perform both the features of the position monitoring system and the scanner alignment control system. Alternatively, the scanning system itself may contain the software and hardware elements necessary to perform the operations of the position monitoring system 608 and the scanner alignment control system 616.

Illustrative Inspection Object

Figure 8:
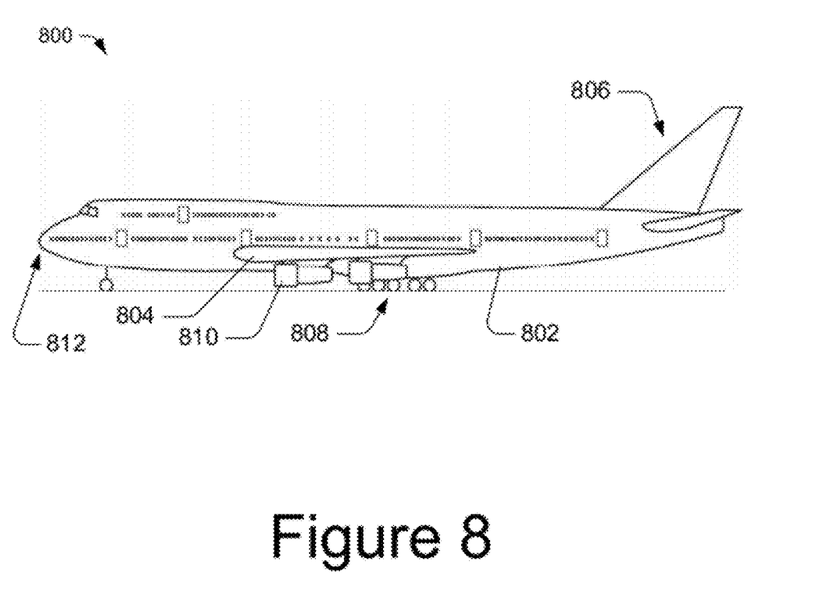
FIG. 8 is a side elevation view of an illustrative aircraft.

FIG. 8 is a side elevational view of an illustrative aircraft 800, which may experience inspection using the techniques disclosed herein. One may appreciate that the aircraft 800 may include various known and unknown parts, particularly if the aircraft has been in-service for many years, such as an aircraft assembled for large-scale war service (e.g., circa 1945, etc.) Thus, the X-ray Back Scattering imaging system may generate an X-ray image to inspect for heel cracks or other sub-surface structural damage.

In this embodiment, the aircraft 800 includes a fuselage 802 including wing assemblies 804, a tail assembly 806, and a landing assembly 808. The aircraft 800 further includes one or more propulsion units 810, a control system 812, and a host of other systems and subsystems that enable proper operation of the aircraft 800. One should appreciate that many parts included in an aircraft may be imaged using the X-ray imaging system techniques disclosed herein.

Although the aircraft 800 shown in FIG. 8 is generally representative of a commercial passenger aircraft; the teachings of the present disclosure may be applied to the maintenance, manufacture, and assembly of other structures including passenger aircraft, fighter aircraft, cargo aircraft, rotary aircraft, other types of manned or unmanned aircraft, ground vehicles, ships, petrochemical facilities, power generation facilities, nuclear facilities, water treatment plants, etc. . . .

Conclusion

While embodiments of the disclosure have been illustrated and described, as noted above, many changes can be made without departing from the spirit and scope of the disclosure. Accordingly, the scope of the disclosure is not limited by the disclosure of these embodiments. Instead, the disclosure should be determined entirely by reference to the claims that follow.

What is claimed is:

1. A portable X-ray backscatter imaging system, comprising:
    a microfocus X-ray tube to emit X-rays through a stationary aperture of the X-ray backscatter imaging system at an object under inspection;
    a plurality of solid state detectors to receive one or more scattered X-rays to generate an image of the object under inspection;
    a scanner alignment control system to position the microfocus X-ray tube, wherein the scanner alignment control system generates a virtual representation of a scanning system comprising a microfocus X-ray tube, the virtual representation of the scanning system being in a same coordinate system as the digital model of the object;
    a rotation mechanism to rotate the microfocus X-ray tube about a yaw axis;
    a track system to raster at least the microfocus X-ray tube; and
    a portable hood to enclose the microfocus X-ray tube and the track system against the object under inspection, the portable hood including a plurality of attachment mechanisms to exclusively attach the microfocus X-ray tube and the track system to the object under inspection.

2. The portable X-ray backscatter imaging system of claim 1, wherein one or more suction cups attach the microfocus X-ray tube and the track system to the object under inspection.

3. The portable X-ray backscatter imaging system of claim 1, wherein the portable hood further includes adjustable legs to adjust a distance of the microfocus X-ray tube to the object under inspection.

4. The portable X-ray backscatter imaging system of claim 1, wherein the portable hood includes at least one safety interlock to communicate an alignment indication message such that the microfocus X-ray tube is only operable when the safety interlock communicates a proper alignment indication message.

5. The portable X-ray backscatter imaging system of claim 1, wherein the rotation mechanism rotates the microfocus X-ray tube independently from the plurality of detectors about the yaw axis.

6. The portable X-ray backscatter imaging system of claim 1, wherein the track system rasters at least the microfocus X-ray tube by: (1) translating the microfocus X-ray tube and the plurality of detectors within the portable hood in an X-direction, and (2) translating the microfocus X-ray tube independent from the plurality of detectors within the portable hood in an Y-direction.

7. The portable X-ray backscatter imaging system of claim 1, wherein the track system rasters at least the microfocus X-ray tube by: (1) translating the microfocus X-ray tube and the plurality of detectors within the portable hood in an X-direction, and (2) translating the microfocus X-ray tube and the plurality of detectors within the portable hood in an Y-direction.

8. The portable X-ray backscatter imaging system of claim 1, further comprising a microfocus X-ray positioning module to analyze pre-defined geometry of the object under inspection and automatically translate the microfocus X-ray tube along the track system to a desired coordinate location of the object under inspection based on the analyzed pre-defined geometry.

9. A method of inspecting a structure for internal damage, the method comprising:
    attaching an X-ray imaging system to the structure at a potentially damaged area of the structure, a portable hood enclosing the X-ray imaging system against the structure;
    generating a virtual representation of a scanning system comprising a microfocus X-ray tube, the virtual representation of the scanning system being in a same coordinate system as a digital model of the object;
    rastering a microfocus X-ray tube of the X-ray imaging system via a plurality of motors of a track system;
    emitting X-rays at the structure through a stationary aperture of the X-ray imaging system; and
    receiving scattered X-rays from the structure to generate an image of the structure.

10. The method of claim 9, wherein a plurality of suction cups attach the X-ray Back Scattering imaging system to the structure.

11. The method of claim 9, wherein the rastering the microfocus X-ray tube includes:
    translating the microfocus X-ray tube and the detector array along the track system in an X-direction; and
    translating the microfocus X-ray tube and the detector array along the track system in a Y-direction.

12. The method of claim 9, wherein the rastering the microfocus X-ray tube includes:
    translating the microfocus X-ray tube and the detector array along the track system in an X-direction; and
    translating the microfocus X-ray tube along the track system in a Y-direction while the detector array remains stationary.

13. The method of claim 9, further comprising:
    analyzing a pre-defined geometry of the structure under inspection to identify a coordinate location of the potentially damaged areas as well as to identify an ideal X-ray incident angle to inspect the potentially damaged area; and
    rotating the microfocus X-ray tube about a yaw axis to the ideal X-ray incident angle,
    wherein the rastering the microfocus X-ray tube automatically rasters the microfocus X-ray tube at the coordinate location.

14. The method of claim 9, further comprising rotating the microfocus X-ray tube about a yaw axis independently from the detector array to adjust an angle at which the emitted X-rays contact the structure.

15. The method of claim 9, further comprising adjusting a length of a plurality of legs of the portable hood to adjust a distance from the microfocus X-ray tube to the structure.

16. The method of claim 9, further comprising communicating an alignment indication message indicating whether the portable hood is correctly attached to the structure.

17. A vehicle inspection system, comprising:
    a portable X-ray backscatter imaging unit, the portable X-ray backscatter imaging unit including:
        a microfocus X-ray tube to emit X-rays at the vehicle;

a scanner alignment control system to position the microfocus X-ray tube, wherein the scanner alignment control system generates a virtual representation of a scanning system comprising a microfocus X-ray tube, the virtual representation of the scanning system being in a same coordinate system as the digital model of the object a track system to raster at least the microfocus X-ray tube; and a portable hood to enclose the microfocus X-ray tube and the track system against the vehicle.

18. The vehicle inspection system of claim 17, wherein the portable X-ray backscatter imaging unit further includes a rotation mechanism to rotate the microfocus X-ray tube about a yaw axis.

19. The vehicle inspection system of claim 17, wherein the portable hood includes a plurality of attachment mechanism to exclusively attach the portable X-ray backscatter imaging unit to the vehicle.

20. The vehicle inspection system of claim 19, wherein the one or more suction cups attach the portable X-ray backscatter imaging unit to the vehicle.

21. A method of positioning a microfocus X-ray tube with respect to an interior feature of an object, the method comprising:

providing a digital model of the object;

generating a virtual representation of a scanning system comprising a microfocus X-ray tube, the virtual representation of the scanning system being in a same coordinate system as the digital model of the object;

displaying the virtual representation of the scanning system together with the digital model on a display device; and positioning the microfocus X-ray tube at a feature of the object desiring inspection, the microfocus X-ray tube positioned in response to an operator selecting the feature from the display device.

22. The method of claim 21 wherein generating a virtual representation of the scanning system includes measuring a plurality of reference features on both the object as well as the scanning system, wherein the plurality of reference features of the object are at locations identified within an operational manual of the object.

23. The method of claim 21 wherein generating a virtual representation of the scanning system includes performing a best fit analysis of a plurality of reference features measured on the scanning system to a plurality of reference features measured on the object.

* * * * *